United States Patent [19]

Twomey

[11] Patent Number: Plant 7,561

[45] Date of Patent: Jun. 18, 1991

[54] ROSE PLANT NAMED TWODREAM

[75] Inventor: Jerry Twomey, Leucadid, Calif.

[73] Assignee: DeVor Nurseries, Inc., Watsonville, Calif.

[21] Appl. No.: 488,738

[22] Filed: Feb. 26, 1990

[51] Int. Cl.[5] ..... A01H 5/00

[52] U.S. Cl. ..... Plt./18

[58] Field of Search ..... Plt./18, 26

[56] References Cited

U.S. PATENT DOCUMENTS

P.P. 3,749 7/1975 Bryum ..... Plt. 18

P.P. 7,289 8/1990 Meilland ..... Plt. 18

*Primary Examiner*—James R. Feyrer

*Attorney, Agent, or Firm*—Charles W. Rummler

[57] ABSTRACT

A new and distinct greenhouse and garden rose plant particularly distinguished by its continuous and profuse production of very large flowers having, in general, an Empire Rose coloration from Spring to late Fall for greenhouse-garden culture with flowers borne on strong, vigorous, upright stems of medium length on a plant having a vigorous, upright and sturdy growth habit with abundant foliage.

1 Drawing Sheet

BACKGROUND OF THE NEW PLANT

This new variety of rose plant originated as a seedling of a hybrid produced by me at my nursery at Carlsbad, Calif., the parent hybrid resulting from my crossing of the variety Emily Post (U.S. Plant Pat. No. 3,749) as a seed parent with pollen from an unnamed and unpatented seedling growing in my collection of rose plants maintained for breeding purposes; the object of this crossing for the said hybrid being the development of a better producing pink rose plant having improved health and vigor. The selected seeding appeared very well to achieve my objectives and accordingly, I propagated that seedling by means of cuttings as well as by budding at the DeVor nurseries at Pleasanton, Calif. with very satisfactory results and at my direction, such propagation was continued through several successive generations which demonstrated conclusively that the novel characteristics of my selected seedling would hold true from generation to generation and appeared to be firmly fixed. As a result of that accomplishment, propagation is now being carried on by DeVor Nurseries, Inc. at Orland, Calif.

DESCRIPTION OF THE DRAWING

My new rose plant is illustrated by the accompanying photographic drawing which in full color shows a face view of a fully opened bloom demonstrating the flower form and the nature of its petals, the colors shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse and out of doors at DeVor Nurseries at Pleasanton, Calif., the color designations specified herein being accoridng to The R.H.S. Colour Chart published by The Royal Horticultural Society of London, England.

THE PLANT

Origin: Seedling.

Parentage:

*Seed parent.*—Emily Post (U.S. Plant Pat. No. 3,749).

*Pollen parent.*—A selected unnamed and unpatented seedling from my collection of rose plants grown in nursery at Carlsbad, Calif.

Classification:

*Botanic.*—Rosa.

*Commercial.*—Greenhouse and Garden Rose.

Form: Upright garden rose bush.

Height: About 70 to 110 cm.

Growth habit: Vigorous, upright and free branching.

Cane:

*Length.*—About 32 cm. to 34.5 cm. from last flower cut.

*Color.*—Yellow Green, 46-A.

Foliage:

*Quantity.*—Abundant.

*Number of leaves.*—About 3 to 5.

*Size of leaves.*—About 86 mm. long and 55 mm. wide.

*Leaflets.*—Number: 3 to 5. Size: About 54 mm. long and about 32 mm. wide. Shape: Oval with denticulate margin. Texture: Slightly leathery. Aspect: Smooth and semi-glossy. Color of leaflets: Upper side — Yellow Green 147-A. Under side — Yellow Green 147-B.

*Stipules.*—Adnate and hairy.

*Rachis.*—About 53 to 58 mm. long for 3 part leaf; about 64 to 67 mm. long for 5 part leaf.

*Petioles.*—About 10 to 18 mm. long.

Ribs and veins: Slightly depressed on top side and slightly rounded on the under side.

Thorns: Declining and varying in size with a length of about 8 mm.

*Color.*—Greyed with 156-B.

THE BUD

Size: Medium.

*Diameter.*—About 26 mm.

*Length.*—About 39 mm.

Shape: Slender, tapering and pointed.

Rate of opening: Moderate.

Color of petals:

*When sepals first divide.*—Rhodomite Red 51-A.

*When petals begin to unfurl.*—Delft Rose 47-C.

Sepals:
*Number.*—Five.
*Shape.*—Spreading with small leafs protruding from sides.
*Character.*—The sepals curl back when flowers open.
*Color.*—Inside — Yellow Green 148-C, with base of Greyed Purple 183-C and covered with Whiteish hairs. Outside — Greyed Purple 183-A with Yellow Green 144-A at the base.

Calyx:
*Shape.*—Funnel shaped.
*Width.*—About 12 mm.
*Length.*—About 9 mm.
*Size.*—Medium.
*Splitting.*—Calyx does not split.
*Aspect.*—Smooth.

Flower stem:
*Length.*—About 70 to 91 mm. with tiny prickles.
*Character.*—Erect and slender.
*Color.*—Greyed Purple 183-C.

THE FLOWER

Blooming habit: Continuous and profusely from Spring through mid-season and Fall, blooming freely under natural conditions through Fall.

Size of bloom: Very Large.
*Diameter.*—About 112 mm.
*Depth.*—About 47 mm.

Borne: Singly on strong, upright stems.

Flower stem:
*Length.*—About 70 to 91 mm.
*Character.*—Sturdy and upright.
*Color.*—Greyed Purple 183-C.

Form:
*When bloom first opens.*—Cup shaped with high center.
*When bloom matures.*—the petals are very nicely imbricated.

Petalage:
*Number.*—26 to 30.
*Number of florets.*—About 4.
*Arrangement.*—Nicely imbricated.
*Form.*—Somewhat cupped with ruffled and lobed margins, and slightly lobed apex.
*Texture.*—Leathery but soft.
*Appearance.*—Satiny and somewhat velvety.
*Color.*—Outer petals — Spinel Red 54-D with the edges somewhat darker and a base of Green Yellow 1-C. Reverse side — Rhodamine Pink 62-A. Inside petals — Empire Rose 48-D with Dawn Pink 49-A around the margins. Reverse side — Red 55-B.

Petaloids:
*Number.*—4.
*Size.*—About 13 mm.
*Color.*—Crimson 52-A with a base of Yellow Orange 15-D.

Flower stem:
*Length.*—About 70 to 91 mm.
*Color.*—Greyed Purple 183-C.
*Character.*—Upright and fairly sturdy.

Fragrance: Semi-strong musk.

Persistence: The flower does hang on and dry.

Discoloration after full bloom: The flower discolors slightly.

Disease resistance: Moderately resistant to mildew, rust, and black spot as observed at Watsonville, Calif.

Lasting quality: Long lasting on the plant and somewhat less lasting as a cut flower.

THE REPRODUCTIVE ORGANS

Stamens:
*Number.*—About 135.
*Arrangement.*—Introrse.
*Anthers.*—Size: About 3 mm. Color: Yellow Orange 22-A around edges, Yellow Orange 16-C inside.
*Filaments.*—Length: About 12 mm. Color: Red 39-B for inside threads changing to 37-B on outside threads.
*Pollen.*—Color: Yellow Orange 22-A around edges, Yellow Orange 16-C inside.

Pistils:
*Number.*—About 131.
*Styles.*—Length: About 12 to 14 mm. Color: Red 54-A on top half which fades into Yellow Green 145-D.
*Stigmas.*—Color: Yellow Orange 20-A.

Character of the ovaries: Oblong, narrowing with rounded edges and covered with silvery hairs.

I claim:

1. The new and distinct rose variety substantially as herein shown and described, characterized by its profuse and continuous production of very large blossoms having a primary color appearance of Empire Rose bordered by large outside petals of a Spinel Red color; the plant having a vigorous, upright and free branching growth habit with abundant foliage.

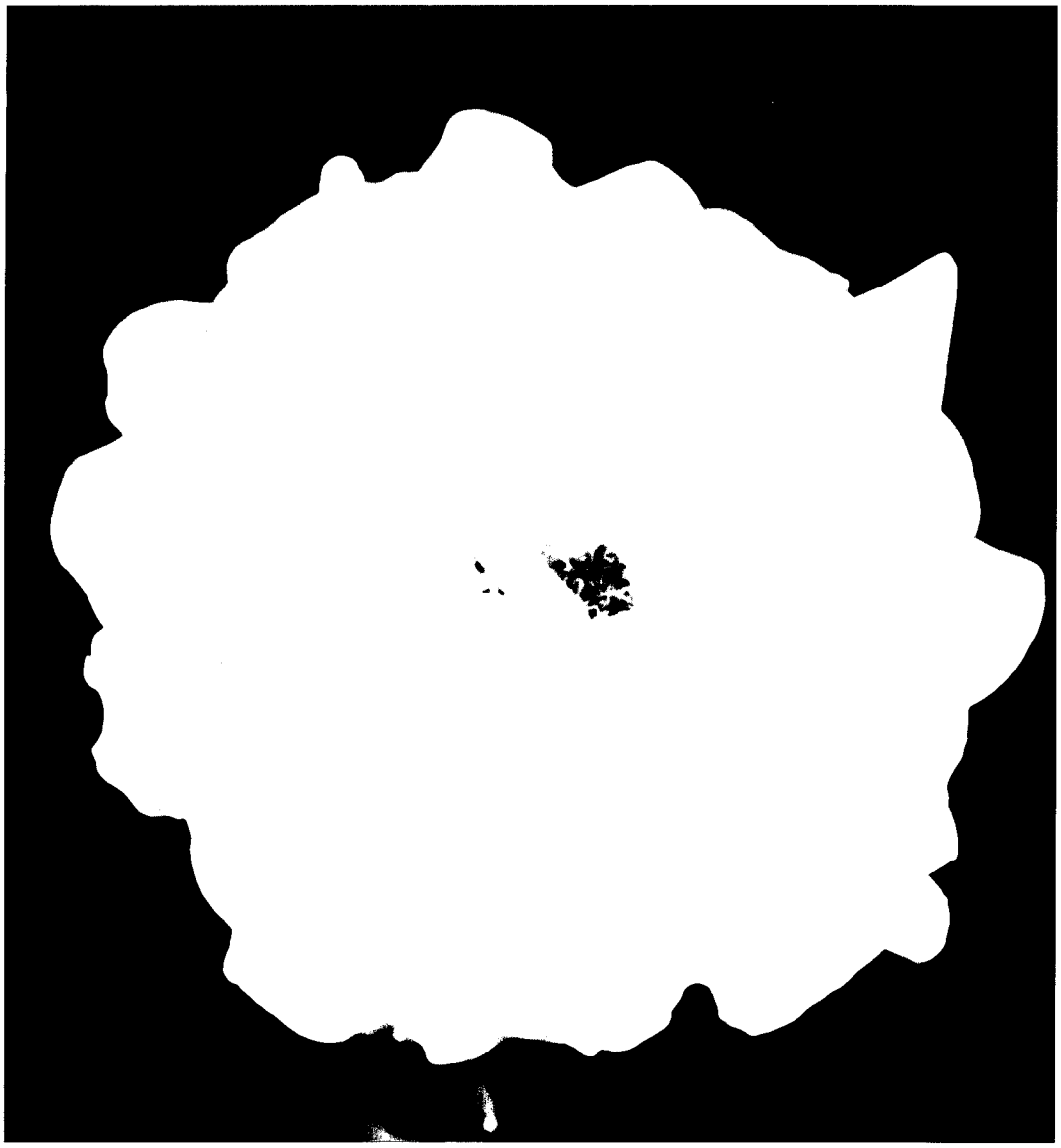

* * * * *